United States Patent
Gooch

Patent Number: 5,403,262
Date of Patent: Apr. 4, 1995

[54] MINIMUM ENERGY TINNITUS MASKER

[75] Inventor: Timothy D. Gooch, Cordova, Tenn.

[73] Assignee: Microtek Medical, Inc., Columbus, Miss.

[21] Appl. No.: 28,326

[22] Filed: Mar. 9, 1993

[51] Int. Cl.[6] .............................................. A61B 5/00
[52] U.S. Cl. .................................... 600/28; 128/746; 607/55
[58] Field of Search ............................ 600/26–28; 128/746; 607/55

[56] References Cited

U.S. PATENT DOCUMENTS

| | | | |
|---|---|---|---|
| 2,753,397 | 7/1956 | Zwislocki | 179/1 |
| 3,394,698 | 7/1968 | Calkins | 128/1 |
| 3,647,968 | 3/1972 | Arguimbau et al. | 179/1 |
| 4,027,264 | 5/1977 | Gutleber | 328/167 |
| 4,031,320 | 6/1977 | Brand et al. | 179/1 |
| 4,222,393 | 9/1980 | Hocks et al. | 128/746 |
| 4,375,061 | 2/1983 | Shoff | 340/384 |
| 5,076,281 | 12/1991 | Gavish | 128/721 |
| 5,167,236 | 12/1992 | Junker | 128/746 |

FOREIGN PATENT DOCUMENTS 2055020  7/1980  United Kingdom .

OTHER PUBLICATIONS

Juergen Tonndorf, "The Origin of Tinnitus", *Tinnitus: Diagnosis/Treatment*, Abraham Shulman Ed. 1991 pp. 41–49.

Jack A. Vernon, "Common Errors in the Use of Masking for Relief of Tinnitus", *Tinnitus: Diagnosis/Treatment*, Abraham Shulman Ed. 1991, pp. 50–66.

Abraham Shulman, "Instrumentation", *Tinnitus: Diagnosis/Treatment*, Abraham Shulman Ed. 1991, pp. 503–513.

Charles S. Watson, et al., "Committee on Hearing, Bioacoustics, and Biomechanics–Tinnitus, Facts, Theories, and Treatments", *U.S. Department of Commerce, National Technical Information Service*, Nov. 1982.

Primary Examiner—Lee S. Cohen
Assistant Examiner—John P. Lacyk
Attorney, Agent, or Firm—Baker & Botts

[57] ABSTRACT

A tinnitus masking device and method for producing a masking signal with a selected center frequency, selected bandwidth, and selected volume is provided. A random noise generator and a clock circuit are employed in conjunction with a switched capacitance filter bank to produce a masking signal with the selected center frequency and selected bandwidth. The masking signal is then received by a volume control unit and then amplified for delivery to the tinnitus sufferer's ear or ears by speakers or headphones. Additionally, the tinnitus masking device may include a timer and fade out unit.

30 Claims, 4 Drawing Sheets

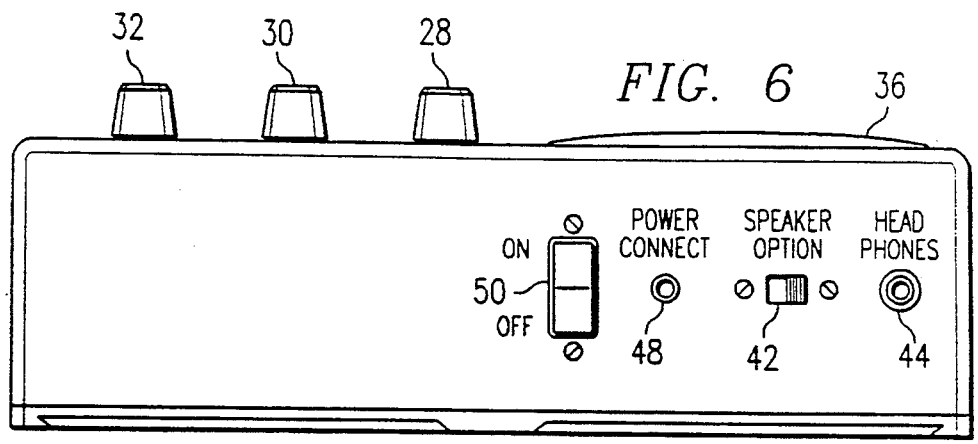
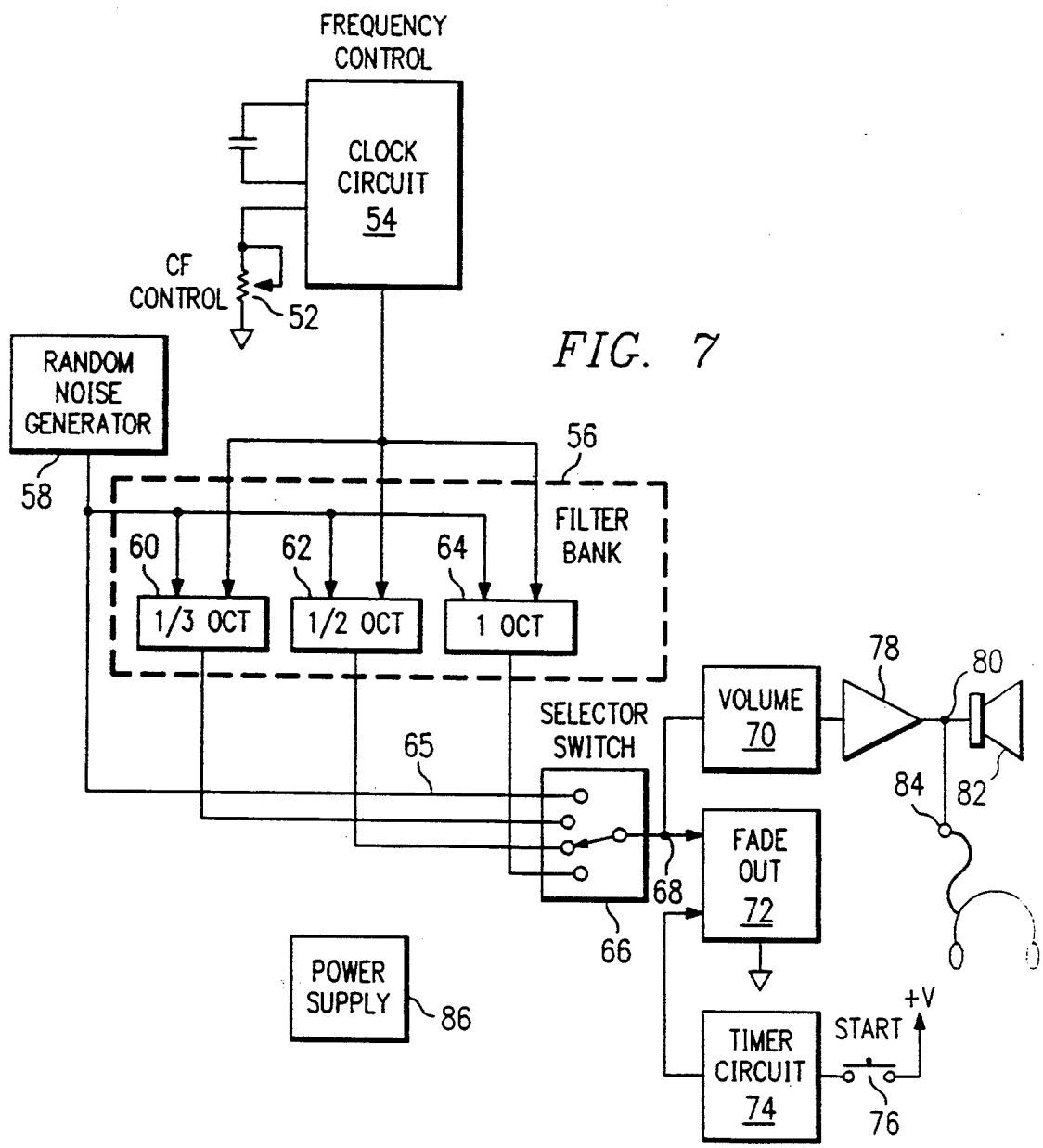

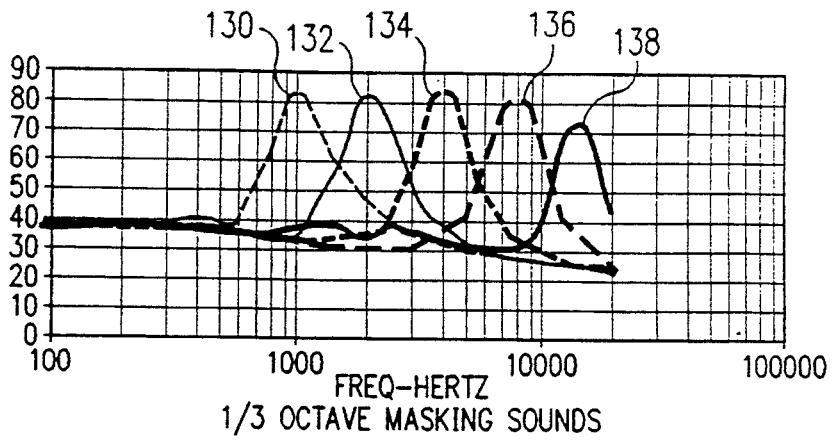
FIG. 10 1/3 OCTAVE MASKING SOUNDS
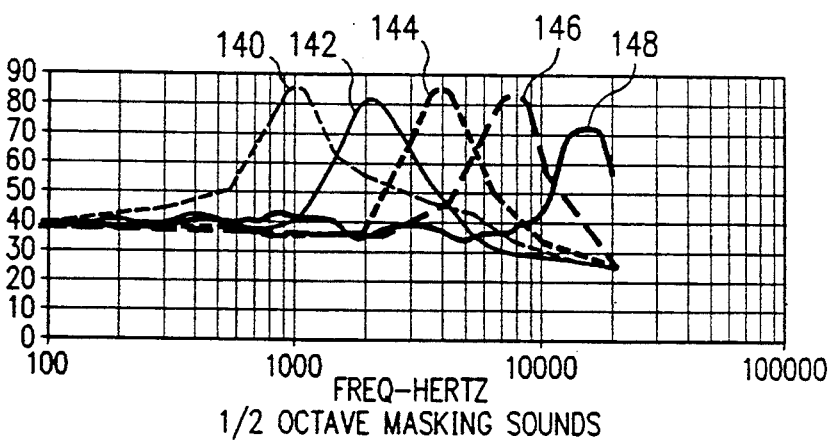
FIG. 11 1/2 OCTAVE MASKING SOUNDS
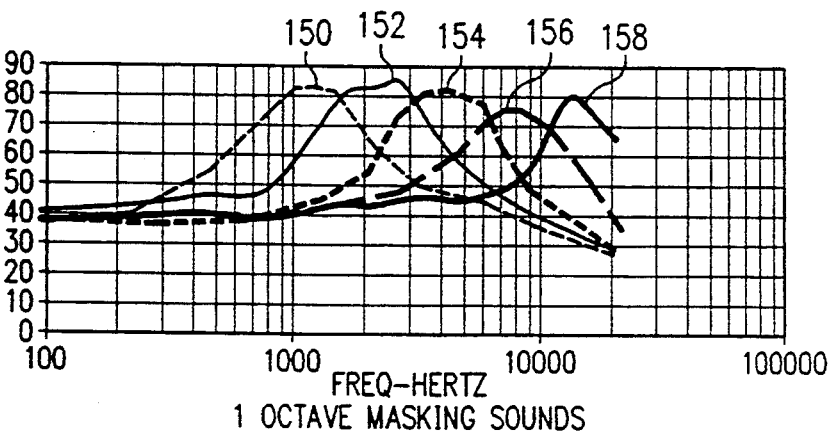
FIG. 12 1 OCTAVE MASKING SOUNDS
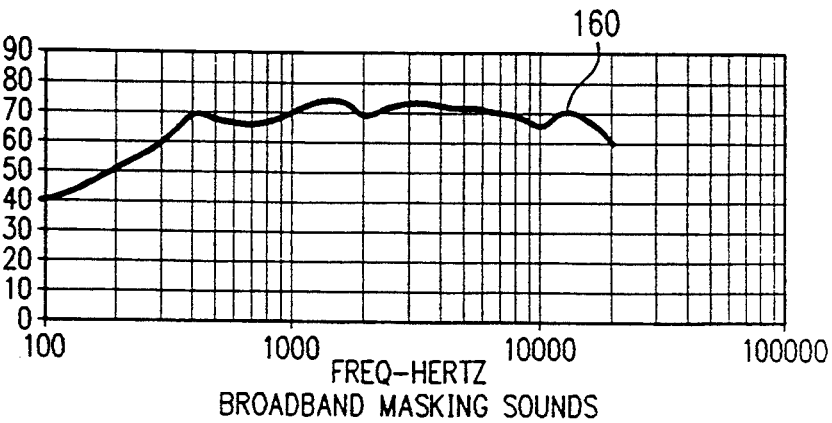
FIG. 13 BROADBAND MASKING SOUNDS

MINIMUM ENERGY TINNITUS MASKER

TECHNICAL FIELD OF THE INVENTION

This invention relates to masking devices, and more particularly, but not by way of limitation, to a minimum energy masker for use by sufferers of subjective tinnitus.

BACKGROUND OF THE INVENTION

Tinnitus describes a perceived sound, e.g., ringing, buzzing, whistling, or roaring, that is experienced by a tinnitus sufferer and that does not exist as a physical sound. The condition can be annoying or very painful, and the discomfort caused by tinnitus frequently interferes with a sufferer's sleep. Tinnitus often occurs at a specific frequency or over a small frequency range and is frequently constant; however, the specific frequency or small frequency range varies from patient to patient.

Most of the relatively recent efforts to treat tinnitus have involved attempts to mask the perceived sound. Masking is the interference of one sound on another. Perfect tinnitus masking involves providing a masking signal that exactly overrules the perceived sound in terms of psychoacoustics without supplying unnecessary energy to the tinnitus sufferer. See e.g., Tinnitus: Diagnosis/Treatment 55 (Abraham Shulman ed. 1991).

Many conventional tinnitus maskers produce only a broad band masking noise or signal. The masking signal produced by these conventional maskers is elevated to a level adequate to mask the tinnitus, but the energy supplied to the tinnitus sufferer's ear is considerably in excess of the required amount. Even if a masker is custom made to be near the sufferer's tinnitus frequency, the broad masking signal supplies energy at many other frequencies as well.

In 1981, the Committee on Hearing, Bioacoustics, and Biomechanics of the National Academy of Science presented characteristics that the committee felt were needed in future tinnitus maskers. The recommendations included a masker that would use narrow bands of noise to reduce the energy delivered, that would match the tinnitus frequency, and that would include a variable bandwidth for the masking frequencies. See H. Sauberman, *Report on Tinnitus Working Group No. 89 of CHABA*, Second International Tinnitus Seminar 250–52 (A. Shulman, J. Ballantine, and J. Laryngol eds. suppl. 1981).

Thus a need has arisen for a tinnitus masker that uses a minimal amount of energy, that allows for a variable center frequency of the masking signal over the human auditory spectrum including high frequencies, and that provides for variable bandwidth selection.

SUMMARY OF THE INVENTION

In accordance with the present invention, the disadvantages and problems associated with previously developed tinnitus maskers and masking techniques have been substantially reduced or eliminated by use of the present invention. Tinnitus masking is carried out by providing a masking signal at a center frequency that may be adjusted to accommodate the frequency of the sufferer's tinnitus. The masking signal may be restricted to a specified bandwidth, and the volume of the masking signal controlled. Thus, a minimum amount of energy may be supplied to overcome the tinnitus.

In accordance with one aspect of the present invention, a broad band signal is delivered to a series of switched capacitance filters. The switched capacitance filters work in conjunction with a circuit clock to produce a signal of a specified center frequency and bandwidth.

In accordance with another aspect of the present invention, the center frequency and bandwidth of the masking signal may be adjusted by a selector. The masking signal is then conditioned in terms of signal strength and delivered to the tinnitus sufferer's ear or ears.

In accordance with another aspect of the present invention, a signal possessing the desired bandwidth may be digitally sampled and then replayed later at a specified rate. The specified rate corresponds to the selected center frequency.

In accordance with yet another aspect of the present invention, a signal processor is provided that produces a digital signal with a specified bandwidth and frequency in response to a digital signal that corresponds to the desired center frequency and a digital signal that corresponds to the desired bandwidth. The digital signal produced by the signal processor is converted into an analog signal and then conditioned for delivery to the sufferer's ear or ears.

In accordance with yet another aspect of the present invention, a timer with a fade out unit is supplied to the tinnitus masker. The timer and fade out unit limit the time duration of a masking session and at the expiration of the selected time interval subtly remove the tinnitus masking signal.

The present invention has significant technical advantages in that it allows control of the center frequency, bandwidth, and volume of the masking signal. Thus, a minimum amount of energy is supplied to the tinnitus sufferer's ear. The masking device is therefore more comfortable to the tinnitus sufferer.

Yet another significant technical advantage of the present invention is that it allows for timed masking sessions that terminate with the subtle removal of the masking sound. Thus, a tinnitus suffer that only needs masking to fall asleep may use the invention while going to sleep and then not be awakened by the sudden removal of the masking sound.

BRIEF DESCRIPTION OF THE DRAWINGS

For a more complete understanding of the present invention and the advantages thereof, reference is now made to the following description taken in conjunction with the accompanying drawings:

FIG. 6 is an elevation view of the embodiment of the present invention shown in FIG. 2;

FIG. 7 is a block diagram representing one embodiment of the present invention;

FIG. 10 is a graphical representation of data developed in a test of one embodiment of the present invention for a ⅛ octave bandwidth and several selected center frequencies;

FIG. 11 is a graphical representation of data developed in a test of one embodiment of the present invention of a ½ octave bandwidth and several selected center frequencies;

FIG. 12 is a graphical representation of data developed in a test of one embodiment of the present invention for a one octave bandwidth and several selected center frequencies; and FIG. 13 is a graphical representation of data developed in a test of one embodiment of the present invention for a broad bandwidth masking signal.

DETAILED DESCRIPTION OF THE INVENTION

Figure 1:
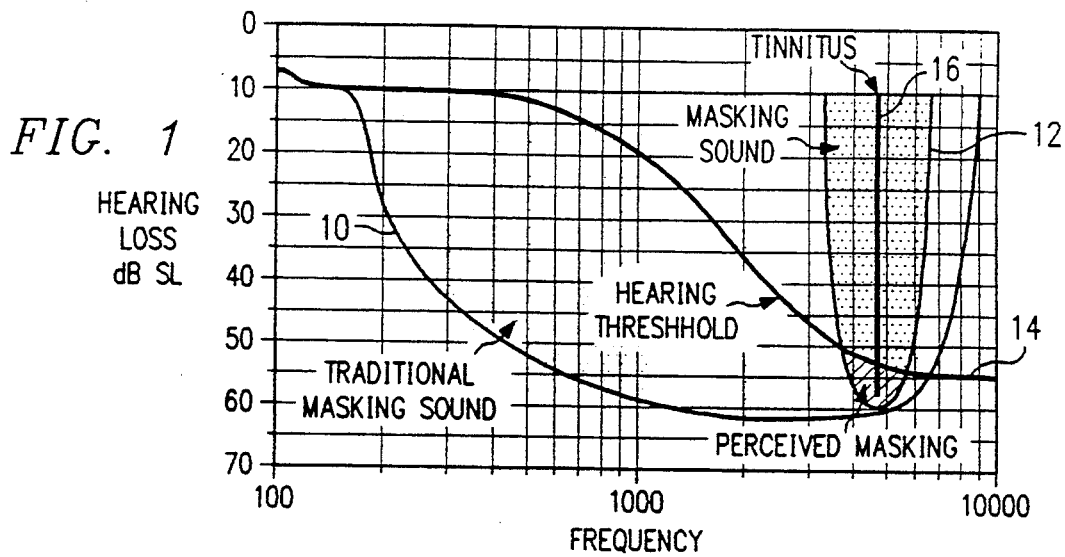
FIG. 1 is a graphical representation of a patient's typical audiogram with a typical conventional masking signal and a masking signal of one embodiment of the present invention superimposed thereon.

Referring to FIG. 1, there is shown a graphical representation of what a typical audiogram of a patient with tinnitus might be, what a traditional masking signal (curve 10) might be, and what a masking signal for one embodiment (curve 12) of the present invention might be. The patient's hearing threshold is indicated by curve 14, an the patient's tinnitus is at approximately 4800 Hz as shown by line 16. The area above curve 10, the curve for a traditional masking sound, represents the amount of energy supplied to the patient's ear by a typical conventional masker. The area above curve 12 represents the energy that might be supplied by one embodiment of the present invention.

As can be seen in FIG. 1, conventional maskers supplied a large quantity of excess energy; substantially all the energy represented by the area between curve 10 and curve 14 is excessive energy. The present invention masks the tinnitus with a minimum amount of energy to the patient; thus, only the area formed by the intersection of curve 14 and curve 12 is energy perceived by the patient.

FIG. 1 shows that a masking signal 12 with a center frequency corresponding to the frequency of the tinnitus 16 and with a small bandwidth supplies only a minimum amount of energy to the tinnitus sufferer's ear or ears. Center frequency refers to the frequency about which a signal is centered; for example the center frequency of the masking signal shown by curve 12 is the same as the tinnitus, line 16. The bandwidth refers to the frequencies included in the signal and that are to either side of the center frequency.

Figure 2:
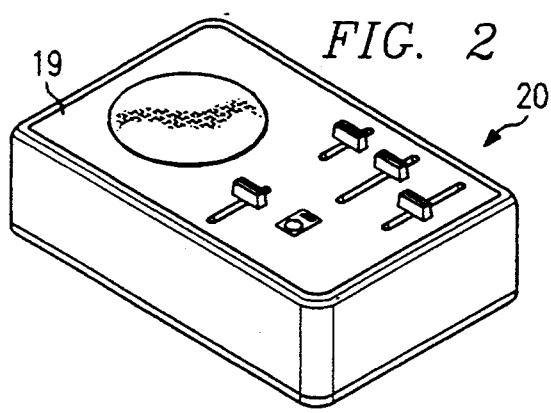
FIG. 2 is a perspective view of one embodiment of the present invention.
Figure 3:
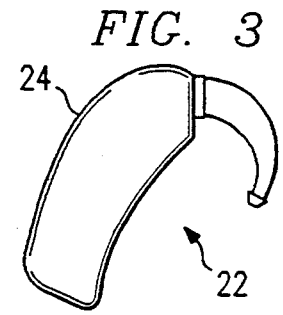
FIG. 3 is a perspective view of one embodiment of the present invention.
Figure 4:
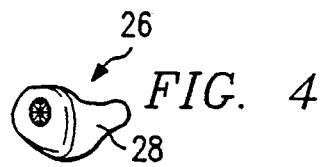
FIG. 4 is a perspective view of one embodiment of the present invention.

Several embodiments of the present invention are shown in FIGS. 2 through 4. FIG. 2 shows a portable, counter top embodiment. This embodiment is explained in more in detail in conjunction with FIGS. 5 and 6. FIG. 3 shows an embodiment that is an over-the-ear tinnitus masker 22. The tinnitus masker 22 has a body or shell 24. As will be described in more detail later, body 24 of masker 22 holds components that allow for a masking signal to be produced with a controllable and continuously variable frequency and volume as well as a variable bandwidth. FIG. 4 shows one embodiment of the tinnitus masker 26 that fits in the wearer's ear. Masker 26 has body or shell 28 formed to allow the device to fit in the wearer's ear. As will be described in more detail later, the body or shell 28 holds components that allows for a variable center frequency, bandwidth, and volume of a masking signal.

Figure 5:
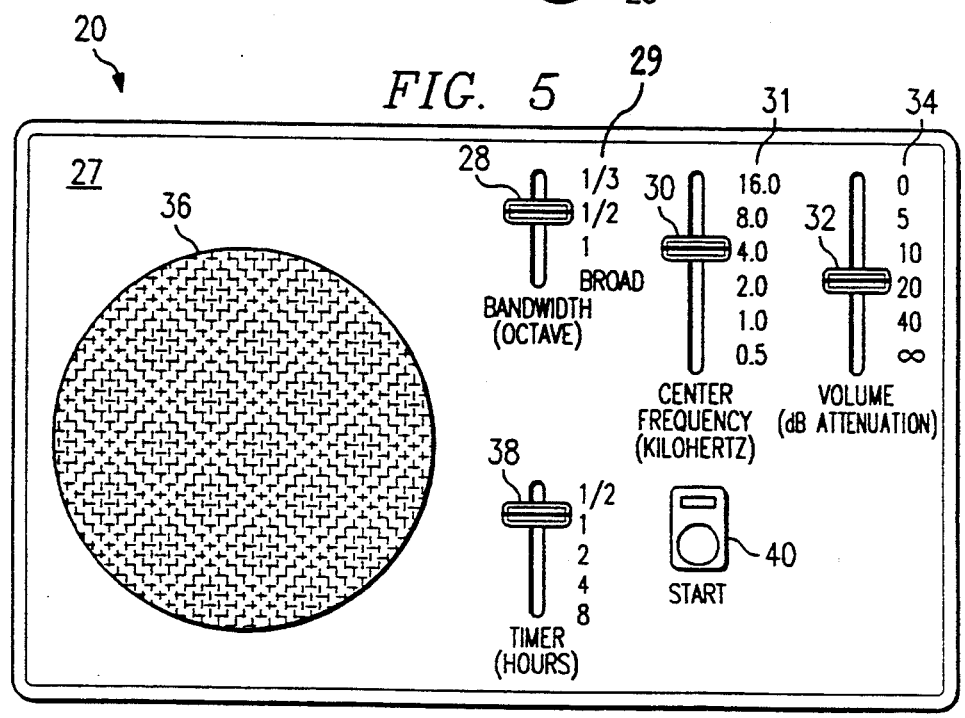
FIG. 5 is a plan view of the embodiment of the present invention shown in FIG. 2.

Referring now to FIG. 5, a plan view of one embodiment of the present invention is shown. Control panel 27 has various controls for the adjustment of the tinnitus masking device 20. Bandwidth selector 28 allows for four selections as shown by reference marks 29: ⅛ octave bandwidth, ½ octave bandwidth, 1 octave bandwidth, and broad bandwidth. Each selection specifies the desired (selected) bandwidth about the center frequency. For example, placing the selector on ½ bandwidth will produce a signal at the center frequency selected that has a bandwidth of ½ octave. If "broad" bandwidth is selected, the masker 20 basically takes random noise and amplifies the spectrum, and thus, produces a broad band masking signal. A broad band signal contains all the frequencies that may be necessary for masking a patient's tinnitus. Other embodiments may include other or additional bandwidth selections. Adjacent to bandwidth selector 28 is center frequency selector or control 30.

Center frequency control or selector 30 allows for the election of a desired (selected) center frequency; the center frequency is continuously variable between 500 and 16,000 Hz. The center frequency control 30 only has effect if the bandwidth selector is on 1, ½, or ⅛ octave bandwidth selection. The reference marks 31 shown on control panel 27 adjacent to center frequency control 30 are for reference. Adjacent to center frequency control 30 is volume control or adjustor 32.

Volume control or selector 32 allows for the attenuation, or adjustment of the energy level, of the masking signal over the range 0 to 95 db. The volume control 32 has reference markings 34 adjacent to it. The tinnitus masker 20 is designed to be read in terms of decibels of attenuation and sound pressure level. When the volume control is placed on the reference marking 34 labeled "0" the masking signal is at its loudest, which is 90 dB at a distance of one foot from speaker 36. When the volume control is placed on the reference "∞", the masking signal corresponds to 0 dB at one foot from speaker 36.

Timer selector 38 allows for the selection of a time interval for the masking session. The options that may be selected with timer selector 38 include ½, 1, 2, 4, 8 hours. Adjacent to timer selector 38 is start switch 40.

Start switch 40 provides a means for the user of the tinnitus masker 20 to signal the tinnitus masker 20 that he or she is ready to begin a masking session. When ready to begin a session, the user presses the start switch 40.

The masking signal may be delivered in several ways to the patient's ear or ears, e.g., by external speakers or headphones. Speaker 36 is located on control panel 27 and delivers the masking signal to the patient's ear. The patient may choose to use headphones as an alternative method. Referring to FIG. 6, headphone jack 44 and speaker option selector 42 may be seen. The patient may choose with option selector 42 to use the speaker 36 or choose to use headphones 46 (not shown) to receive the masking signal. If the latter is desired, the patient moves speaker option selector 42 toward headphone jack 44 and connects headphones 46 to headphone jack 44. Other means of delivering the masking signal to the patient may be used as well; for example, using a low power transmitter or an electromagnetic coil to deliver the signal from the tinnitus masker 20 to a receiver worn in or on the sufferer's ear.

FIG. 6 also shows power connector 48 and power switch 50. An external power source is connected to the tinnitus masker 20 at the power connector 48. The embodiment shown uses a 12 volt DC power supply and is powered up by selecting the "ON" position with power switch 50.

Numerous circuit designs may be incorporated as part of tinnitus masker 20, 22, or 26 to produce the masking signal of desired center frequency, bandwidth, and sound pressure level. One embodiment of the present invention that will produce the desired masking signal is shown in FIG. 7. The desired or predetermined center frequency is selected with center frequency control or selector 30 (FIG. 5) which, at the circuit level, corresponds to center frequency control potentiometer 52. Potentiometer 52 controls the discharge current of clock circuit 54 corresponding to the desired center frequency. Clock circuit 54, e.g., Exar model 2209, develops a center frequency signal corresponding to the desired center frequency that is delivered to a switched capacitance filter bank 56. Pseudo-random noise generator 58, e.g., National Semiconductor model 5437N, produces pseudo-random noise by generating variable width pulse trains that have a frequency spectrum of equal energy throughout all frequencies. The signal produced by random noise generator 58 is delivered to switch capacitance filter bank 56.

Switch capacitance filter bank 56 is formed by a plurality of switched capacitance filters. The embodiment shown in FIG. 7 contains 3 such filters: a first switched capacitance filter 60 that will filter a signal such that it will have a ⅛ octave bandwidth about a center frequency; a second switched capacitance filter 62 that will filter a signal such that it will have a ½ octave bandwidth about a center frequency; and a third switched capacitance filter 64 that will filter a signal such that it will have a one octave bandwidth about a center frequency. The signal produced by clock circuit 54 and the signal produced by random noise generator 58 are received by each of the switched capacitance filters 60, 62, and 64. The switch capacitance filters 60, 62, and 64 produce a signal corresponding to the selected center frequency and a selected or predetermined bandwidth which is associated with each switched capacitance filter 60, 62, and 64. The signals produced by each of these capacitance filters 60, 62, and 64 are delivered to bandwidth selector switch 66. Additionally, random noise generator 58 delivers an unfiltered signal (path 65) to selector switch 66.

The desired bandwidth is selected with selector switch 66 (selector switch 66 corresponds with bandwidth selector 28 of FIG. 5). A signal that corresponds with the desired center frequency as selected with center frequency control 52 and desired bandwidth as selected with selector switch 66 is delivered to circuit gate 68. Two pathways are presented to the signal as the signal leaves selector switch 66 at circuit gate 68: a first pathway that would deliver the signal to a volume control 70 and a second pathway that would deliver the signal to a fade out unit 72. Fade out unit 72 receives a signal from timer circuit 74. Timer circuit 74, fade out unit 72, and circuit gate 68 allow for a timed masking session that terminates with the subtle or gradual removal of the masking signal.

Timer circuit or timing unit 74 allows a specified or predetermined time interval for a given masking session to be selected with a timer selector (e.g., 38 of FIG. 5). Timer circuit 74 is energized when start switch 76 is depressed which connects a power supply 86 to timer circuit 74. When energized, timer circuit 74 will deliver a signal to fade out unit 72 during the selected time interval. While receiving such a signal from timer circuit 74, the fade out unit will make the pathway from circuit gate 68 to fade out unit 72 appear to have a very high impedance, much higher than the impedance of the pathway from circuit gate 68 to volume control 70. Thus, a signal from selector switch 66 will be delivered to volume control 70 during the selected time interval. When the time interval has expired, fade out unit 72 gradually reduces the perceived impedance of the pathway from circuit gate 68 to fade out unit 72 such that the signal from selector switch 66 will be delivered to fade out unit 72 which will then function to ground the delivered signal. During a masking session, the signal from selector switch 66 is delivered to volume unit or energy level adjustor 70.

Volume unit 70 attenuates, or adjusts, the energy level of the signal to correspond with the desired energy level as selected by the user with a volume control, volume control 32 (FIG. 5). The attenuated or adjusted masking signal is then delivered from volume control unit 70 to amplifier 78. Amplifier 78 further conditions the signal for delivery to the patient's ear. The signal exiting amplifier 78 is delivered to either speaker 82 (36 of FIG. 5) or headphone jack 84 (44 of FIG. 6) which convert the signal to an audio signal or audio output. Audio selector switch or speaker option switch 80 (42 of FIG. 6) determines whether the signal exiting amplifier 78 is delivered to speaker 82 or headphone jack 84.

Power supply 86 delivers power to the components requiring power, clock circuit 54, random noise generator 58, timer circuit 74, and amplifier 78. The embodiment of the invention shown in FIG. 7 utilizes regulated 12 volt and 5 volt power supplies. The circuit components described in connection with FIG. 7 may be contained in a housing such as body or shell 19 (FIG. 2). Shell 19 is a rectangular container formed of a rigid material.

Figure 8:
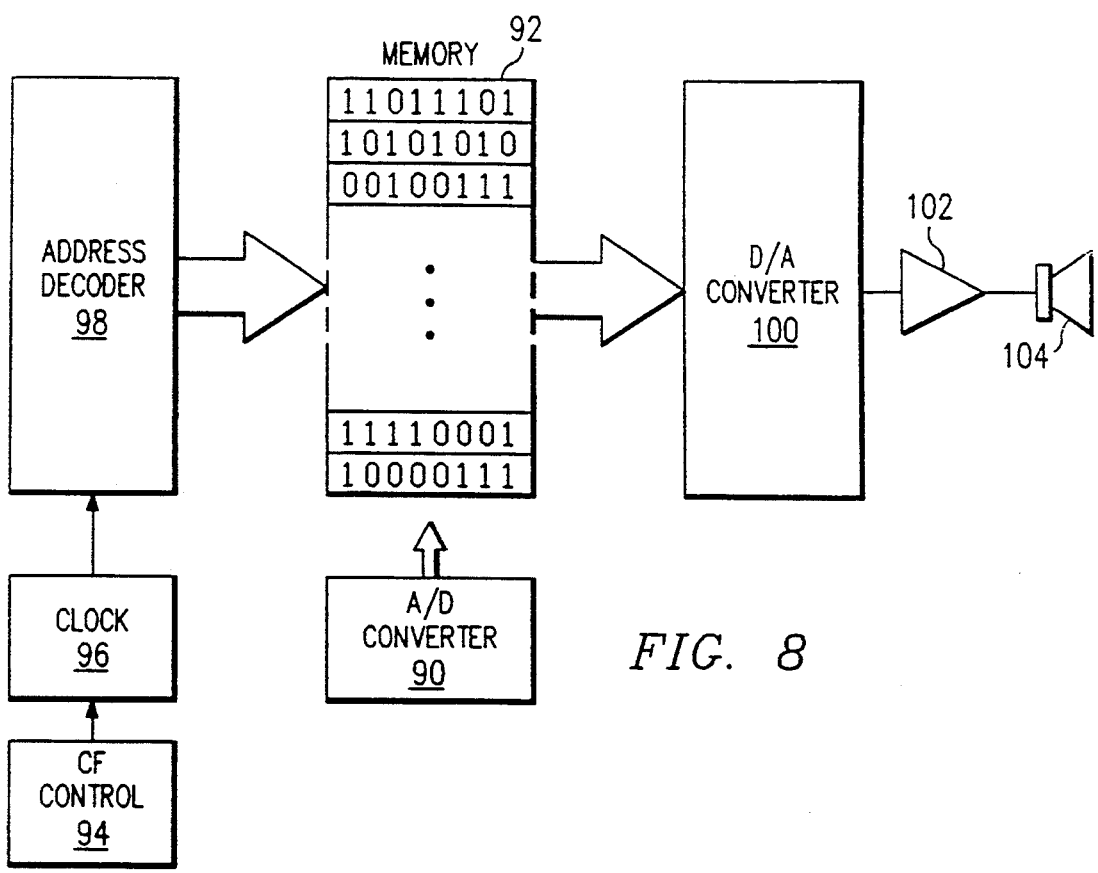
FIG. 8 is a block diagram representing one aspect of one embodiment of the present invention.

Referring now to FIG. 8 there is shown another embodiment of the invention. A predetermined masking signal having the predetermined bandwidth corresponding to a desired bandwidth is produced by an external device, e.g., the device discussed in conjunction with FIG. 5, and is digitally sampled by analog to digital converter 90. Analog to digital converter 90 delivers digital information corresponding to the predetermined signal to memory bank 92. Digital sampling is the process of obtaining a sequence of instantaneous values of a signal or wave. The desired center frequency for the masking signal is selected with center frequency control 94. Center frequency control 94 delivers a center frequency signal to circuit clock 96 corresponding to the desired or selected center frequency. A circuit time interval is then produced by circuit clock 96 in response to the center frequency signal.

Address decoder 98 retrieves the digitized information found in memory bank 92 and develops a digital masking signal corresponding thereto and at a rate that corresponds to the circuit time interval received by address decoder 98 from circuit clock 96. This process of retrieving and producing a masking signal may be referred to as replaying the digital information. The rate that the signals are produced by address decoder 98 in response to the circuit time interval determines the center frequency of the masking signal. The signal produced by the address decoder 98 in conjunction with memory bank 92 is then converted to an analog masking signal by digital to analog converter 100. The analog masking signal developed by digital to analog converter 100 may be delivered to an amplifier 102 and speaker 104, which condition the signal for delivery to the patient's ear or ears. The circuit represented by FIG. 8 may have a volume control or adjustor and timer circuit and fade out unit added analogous to the circuit represented by FIG. 7.

Figure 9:
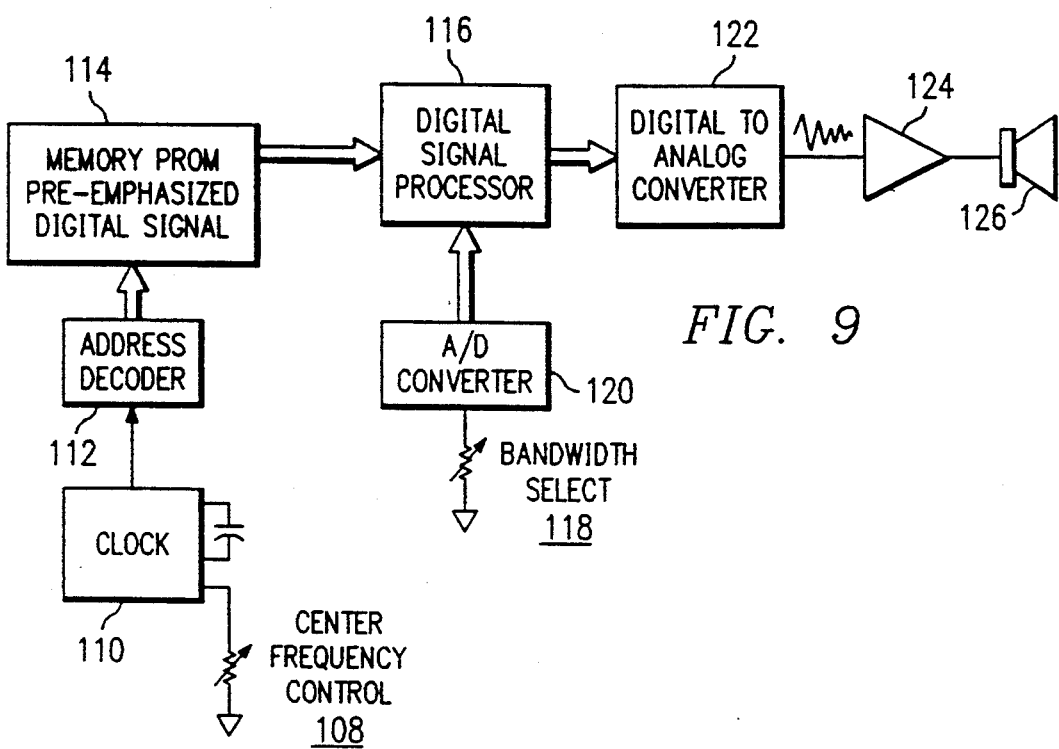
FIG. 9 is a block diagram representing one aspect of one embodiment of the present invention.

Referring now to FIG. 9, there is shown yet another embodiment of the invention. The embodiment shown in FIG. 9 uses a digital signal processor to develop the masking signal. The desired center frequency is selected with center frequency control or selector 108, which may be a potentiometer. The center frequency control 108 produces an analog center frequency signal that corresponds to the selected center frequency. The analog center frequency signal is delivered to circuit clock 110. Circuit clock 110 produces a circuit time interval signal and delivers the time interval signal to address decoder 112 in response to the center frequency signal. Address decoder 112 and memory PROM (programmable read only memory) 114 then operate to deliver a digital signal to digital signal processor 116 that corresponds to an analog masking signal of the selected center frequency. The memory PROM 114 contains digitized information that may be used to develop the broadest bandwidth signal that would be desired. The decoder 112 and PROM 114 may be referred to as a "digital signal unit."

The desired bandwidth for the masking signal is selected with bandwidth selector 118, which may be a potentiometer. Bandwidth selector 118 produces an analog bandwidth signal corresponding to the selected bandwidth. The analog signal produced by bandwidth selector 118 is delivered to analog to digital converter 120 that in turn delivers a digital bandwidth signal corresponding to the selected bandwidth to digital processor 116. Digital signal processor 116 processes the signal delivered from the analog to digital converter 120 and the signal delivered from memory PROM 114 and decoder 98 to produce a digital masking signal that corresponds to an analog masking signal with the selected center frequency and selected bandwidth. The masking signal produced by the digital signal processor 116 is then delivered to a digital to analog converter 122.

Digital to analog converter 122 converts the digital masking signal received from the digital processor 116 into an analog masking signal which is delivered to amplifier 124. Amplifier 124 conditions the analog signal for delivery to the patient's ear. The signal produced by amplifier 124 is then delivered to speaker 126. The circuit represented by FIG. 6 may have added to it a volume control or adjustor and timer and fade out unit analogous to those shown in FIG. 7. The circuit represented by FIG. 9 may be contained in a shell or body as shown in FIGS. 2 through 4.

Referring now to FIG. 10, there is shown a graphical representation of data developed for one embodiment of the present invention. The vertical axis of FIG. 10 represents sound pressure level in decibels and the horizontal axis represents the frequency of the signal in hertz on a logarithmic scale. The data shown in FIGS. 10-13 was developed in an ordinary room and without eliminating background noises. The graph of FIG. 10 shows six signals produced with different center frequencies selected on the continuously variable center frequency control 30 and with a one-third octave band width selection made with the band width selector 28. Curve 130 shows data for a center frequency of approximately 1000 hertz and a band width of one-third octave. Similarly, curves 132, 134, 136 and 138 present data for center frequencies of approximately 2000, 4000, 8000, and 16,000 hertz and a selected band width of one-third octave.

Referring now to FIG. 11, there is shown a graphical representation of test data developed for one embodiment of the present invention. The data presented in FIG. 11 is analogous to the data of FIG. 10, except the data is for masking signals with a one-half octave band width and center frequencies of 1000 (curve 140), 2000 (curve 142), 4000 (curve 144), 8000 (curve 146), and 16,000 hertz (curve 148).

Referring now to FIG. 12, there is shown graphical representation of test data for one embodiment of the present invention. The data presented in FIG. 9 is analogous to the data of FIG. 10, except the data is for a selection of a one octave band width and for center frequencies of 1100 (curve 150), 2100 (curve 152), 4000 (curve 154), 8000 (curve 156), and 16,000 hertz (curve 158).

FIG. 13 is a graphical representation of test data for one embodiment of the present invention. Curve 160 presents data taken when the band width selector 28 is placed on the "broad" position. As previously discussed, the signal delivered when the band width selector 28 is on "broad" is an unfiltered signal encompassing all the frequencies of the operating range for the embodiment.

Although the present invention has been described in detail, it should be understood that various changes, substitutes and alterations can be made herein without departing from the spirit and scope of the invention as defined by the appended claims.

What is claimed is:

1. A tinnitus masking device comprising:
   circuit means for producing a masking signal, said masking signal having a selected center frequency and a selected bandwidth;
   adjusting means for adjusting the energy level of said masking signal to produce an adjusted masking signal; and
   delivering means for delivering said adjusted masking signal to a patient's ear; and
   wherein said circuit means for producing a masking signal further comprises:
     noise generator means for producing a broad band signal,
     a circuit clock,
     a plurality of filter means for filtering said broad band signal from said noise generator means, each of said filter means cooperating with said circuit clock for selecting said center frequency of said broad band signal, and
     means for selecting one of said filter means, such that said masking signal is generated by said selected filter means.

2. A tinnitus masking device comprising:
   a circuit means for producing a masking signal, said masking signal having a selected center frequency and a selected bandwidth;
   adjusting means for adjusting the energy level of said masking signal to produce an adjusted masking signal; and
   delivering means for delivering said adjusted masking signal to a patient's ear; and
   wherein said circuit means for producing a masking signal further comprises:

means for sampling a predetermined signal, and for producing digitized information corresponding to said predetermined signal, said predetermined signal having a predetermined bandwidth, means for storing said digitized information, means for producing a digital signal at a selected rate from said digitized information, and means for converting said digital signal into said masking signal.

3. A tinnitus masking device comprising:

circuit means for producing a masking signal, said masking signal having a selected center frequency and a selected bandwidth;

adjusting means for adjusting the energy level of said masking signal to produce an adjusted masking signal;

delivering means for delivering said adjusted masking signal to a patient's ear; and wherein said circuit means for producing a masking signal further comprises:

a center frequency selector means for producing an analog center frequency signal corresponding to a selected frequency, a circuit clock means for receiving said analog center frequency signal, a digital signal unit cooperating with said circuit clock means for producing a digital center frequency signal at a rate corresponding to said selected center frequency and containing a band of frequencies centered about said center frequency, a bandwidth selector means for selecting a desired bandwidth and for producing a digital bandwidth signal corresponding to said selected bandwidth, a digital signal processor means for receiving said bandwidth signal and said digital center frequency signal and for producing a digital masking signal corresponding to said masking signal, and a digital to analog converter means coupled to said digital signal processor means for generating said masking signal from said digital masking signal.

4. An apparatus for masking tinnitus comprising:

means for producing a broad band signal;

means for centering said broad band signal about a selected frequency;

a plurality of switched capacitance filter means, each of said switched capacitance filter means for filtering said broad band signal to produce a masking signal with a predetermined bandwidth about said predetermined center frequency; and a selector means for selecting one of said plurality of switched capacitance filter means.

5. The apparatus of claim 4, further comprising an amplifier means for amplifying said masking signal for audio output.

6. The apparatus of claim 4, further comprising an adjustor means for receiving said masking signal and producing an adjusted masking signal therefrom.

7. The apparatus of claim 4 wherein said means for producing said signal further comprises a random noise generator.

8. The apparatus of claim 4 wherein said means for centering said signal about a predetermined frequency comprises:

means for producing a voltage input corresponding to a desired centered frequency;

said means for producing a voltage input for controlling a discharge current of said circuit clock corresponding to said desired center frequency;

a clock circuit; and said clock circuit in conjunction with said plurality of switched capacitance filter means for centering said signal at a predetermined frequency in response to said voltage input.

9. The apparatus of claim 8, wherein said means for producing said voltage input comprises a potentiometer.

10. An apparatus for masking tinnitus comprising:

means for digitally recording a predetermined masking signal with a predetermined bandwidth;

means for replaying said digitally recorded masking signal as a digital masking signal at a selected rate corresponding to a selected center frequency;

means for converting said digital masking signal into an analog electrical signal; and means for converting said analog electrical signal into an audio signal.

11. The apparatus of claim 10, wherein said means for converting said analog electrical signal to an audio signal further comprises an energy adjustor control, said energy adjustor control for adjusting the energy level of said audio signal.

12. An apparatus for masking tinnitus comprising:

a center frequency control for selecting a desired center frequency and producing a center frequency signal corresponding to said selected center frequency;

a circuit clock coupled to said center frequency control for receiving said center frequency signal and for producing a circuit time interval in response to said center frequency signal;

a memory bank;

an analog to digital converter coupled to said memory bank for receiving an analog masking signal and converting said analog masking signal into a digital signal and for storing said digital signal in said memory bank;

an address decoder coupled to said circuit clock and said memory bank for developing a digital signal at a rate determined by said circuit time interval and based on said digital signal in said memory bank; and a digital to analog converter coupled to said decoder and memory bank for converting said digital signal from said decoder and memory bank into an analog masking signal.

13. The apparatus of claim 12, further comprising a means for adjusting the masking signal with respect to the masking signal's volume.

14. Apparatus for masking tinnitus comprising:

a center frequency control means for selecting a desired center frequency and to produce a center frequency signal corresponding to said desired center frequency;

a circuit clock means coupled to said center frequency control means for receiving said center frequency signal;

a memory bank for storing digitized information corresponding to an analog broad band masking signal;

an address decoder coupled to said memory bank for, in conjunction with said circuit clock means and said memory bank, producing a digital signal with a specified center frequency;

means for producing a digitized bandwidth signal corresponding to a desired bandwidth;

a digital signal processor means for receiving said digital signal from said decoder and said digital bandwidth signal and to produce therefrom a digital masking signal;

a digital to analog converter means for converting said digital masking signal from said digital signal processor means into an analog masking signal having the desired center frequency and bandwidth; and a means for adjusting the energy level of said analog masking signal.

15. The apparatus of claim 14, further comprising a housing holding the center frequency control means, circuit clock means, memory bank, address decoder, means for producing a digitized bandwidth signal, digital signal processor, and digital to analog converter means.

16. The apparatus of claim 15, wherein said housing comprises a shell formed to fit over a patient's ear.

17. The apparatus of claim 15, wherein said housing comprises a rectangular container formed of a rigid material, said container sized to be portable.

18. The apparatus of claim 15, wherein said housing comprises a shell formed to fit in a patient's ear.

19. Apparatus for masking tinnitus comprising:

a pseudo-random noise generator for producing a broad band electrical signal;

a frequency selector switch allowing selection of a selected center frequency;

a circuit clock coupled to said frequency selector switch and for producing a circuit time interval corresponding to said selected frequency;

a plurality of switched capacitance filters, each of said plurality of switched capacitance filters coupled to said pseudo-random noise generator and said circuit clock and in conjunction with said circuit clock and said pseudo-random noise generator producing a masking signal with a selected center frequency and a predetermined bandwidth; and a bandwidth selector switch coupled to said plurality of switched capacitance filters and for selecting one of said plurality of switched capacitance filters to produce one masking signal.

20. The apparatus of claim 19 and further comprising an amplifier coupled to said bandwidth selector switch for increasing the energy level of said masking signal.

21. The apparatus of claim 19 and further comprising a volume control coupled to said bandwidth selector switch for adjusting the energy level of said masking signal.

22. The apparatus of claim 19 wherein said plurality of switched capacitance filters comprises three switched capacitance filters for producing a one third, one half and one octave bandwidth masking signal.

23. The apparatus of claim 19 further comprising a timing unit coupled to said pseudo-random noise generator for supplying power to said pseudo-random noise generator for a predetermined time period.

24. The apparatus of claim 23 further comprising a fade out unit coupled to said timing unit and said pseudo-random noise generator for gradually decreasing said power to said pseudo-random noise generator over a predetermined time interval when said timing unit terminates the power to said pseudo-random noise generator.

25. A method of masking tinnitus with a masking signal of a selected frequency and selected bandwidth comprising the steps of:

producing broad band signal with a broad band of frequencies;

producing a circuit clock signal;

filtering said broad band signal with a capacitance filter to produce the selected bandwidth;

exciting said capacitance filter with said circuit clock signal to produce the selected center frequency for a masking signal;

adjusting the energy level of said masking signal; and delivering said masking signal to patient's ear.

26. The method of claim 25, wherein the step of producing a broad band signal with a broad band of frequencies comprises electrically exciting a pseudo-random noise generator.

27. The method of claim 25, further comprising the steps of:

selecting a desired time duration for the masking signal; and limiting the time interval for producing said signal according to said desired time duration with a timing unit.

28. A method for masking tinnitus comprising the steps of:

digitally sampling a predetermined masking signal having a predetermined bandwidth produced by an external device;

storing digital information pertaining to said predetermined masking signal in a memory bank;

retrieving said digital information from said memory bank;

producing a digital masking signal from the memory bank at a predetermined rate corresponding to desired center frequency of an analog masking signal;

converting said digital masking signal to an analog masking signal; and conditioning said analog masking signal for delivery to patient's ear.

29. A method of masking tinnitus comprising the steps of:

selecting a selected center frequency:

producing a digital broad band signal with the selected frequency;

selecting a desired bandwidth;

producing a digital bandwidth signal corresponding to said desired bandwidth;

delivering said digital broad band signal and said digital bandwidth signal to a digital signal processor;

processing said broad band digital signal and said digital bandwidth signal with said digital signal processor to produce a digital masking signal corresponding to an analog masking signal with the desired bandwidth and center frequency;

converting said digital masking signal to an analog masking signal; and conditioning said analog masking signal for delivery to patient's ear.

30. An apparatus for masking a patient's tinnitus by developing a masking signal with a minimal amount of energy by using a narrow bandwidth about a selectable center frequency, the apparatus comprising:

clock circuit means for developing a discharge current;

potentiometer means coupled to the clock circuit means for adjusting said discharge current;

a plurality of switched capacitance filters coupled to the clock circuit means and potentiometer means for receiving the discharge current;

noise generating means for producing a broad band electrical noise signal, the noise generating means coupled to the plurality of switched capacitance filters;

each of the plurality of switched capacitance filters receives a portion of the current and the noise signal from the noise generating means and filters the signals to produce a filtered masking signal with a predetermined bandwidth and that corresponds to the discharge current;

a selector coupled to the plurality of switched capacitance filters for selecting one of the plurality of switched capacitance filters and to receive the filtered masking signal therefrom;

a volume unit coupled to the selector attenuating the selected filtered masking signal to a desired level;

means for audio output coupled to the volume unit for receiving the signal therefrom and developing an audio signal for delivery to the patient's ear.

* * * * *

UNITED STATES PATENT AND TRADEMARK OFFICE
CERTIFICATE OF CORRECTION

PATENT NO. : 5,403,262
DATED : April 4, 1995
INVENTOR(S) : Gooch

It is certified that error appears in the above-indentified patent and that said Letters Patent is hereby corrected as shown below:

Column 3, line 53, after "more", delete -- in --;

Column 3, line 65, after "that", delete "allows" and insert -- allow --.

Column 4, line 2, after "selector", delete "28" and insert -- 28' --;

Column 4, line 16, after "selector" delete "28" and insert -- 28' --;

Column 4, line 27, after "control", insert -- adjustor --.

Column 6, line 13, after "volume", insert -- control --;

Column 6, line 15, after "Volume", insert -- control --;

Column 6, line 23, after "which", delete "convert" and insert -- converts --.

Column 7, line 34, after "digital", insert -- signal --;

Column 7, line 38, after "98", insert -- (FIG. 8) --.

Column 7, line 45, after "digital", insert -- signal --;

Column 7, line 62, after "shows", delete "six", insert -- five --;

Column 7, line 65, after "octave", delete "band width" and insert -- bandwidth --;

Column 7, line 66, after "the", delete "band width" and insert -- bandwidth --;

Column 7, line 68, after "and a", delete "band width" and insert -- bandwidth --.

UNITED STATES PATENT AND TRADEMARK OFFICE
CERTIFICATE OF CORRECTION

PATENT NO. : 5,403,262
DATED : April 4, 1995
INVENTOR(S) : Gooch

It is certified that error appears in the above-indentified patent and that said Letters Patent is hereby corrected as shown below:

Column 8, line 9, after "octave", delete "band width" and insert -- bandwidth --;

Column 8, line 13, after "shown", insert -- a --;

Column 8, line 15, after "in", delete "FIG. 9" and insert -- FIG. 12 --;

Column 8, line 17, after "octave" delete "band width" and insert -- bandwidth --.

Column 8, line 23, after "the", delete "band width" and insert -- bandwidth --;

Column 8, line 25, after "when the", delete "band width" and insert -- bandwidth --.

Signed and Sealed this

Ninth Day of January, 1996

Attest:

BRUCE LEHMAN

*Attesting Officer*         *Commissioner of Patents and Trademarks*